(12) United States Patent
Stouffs et al.

(10) Patent No.: US 7,935,190 B2
(45) Date of Patent: May 3, 2011

(54) PROCESS FOR PREPARING MALTITOL ENRICHED PRODUCTS

(75) Inventors: Robert Henri-Marcel Stouffs, Ferrara (IT); Gianfranco Brussani, Ponderano (IT); Riccardo Sacrato, Lendianara (IT); Chad Allen Conard, Ft Calhoun, NE (US); Thomas J. Sasman, Omaha, NE (US)

(73) Assignee: Cargill, Incorporated, Wayzata, MN (US)

( * ) Notice: Subject to any disclaimer, the term of this patent is extended or adjusted under 35 U.S.C. 154(b) by 1179 days.

(21) Appl. No.: 10/564,652

(22) PCT Filed: Jul. 6, 2004

(86) PCT No.: PCT/EP2004/007372
§ 371 (c)(1),
(2), (4) Date: Jan. 13, 2006

(87) PCT Pub. No.: WO2005/014608
PCT Pub. Date: Feb. 17, 2005

(65) Prior Publication Data
US 2006/0188626 A1  Aug. 24, 2006

(30) Foreign Application Priority Data
Jul. 18, 2003  (EP) .................................... 03254528

(51) Int. Cl.
*C13K 13/00* (2006.01)
(52) U.S. Cl. ........................................ 127/46.2; 435/95

(58) Field of Classification Search ............... 127/46.2; 435/95
See application file for complete search history.

(56) References Cited

U.S. PATENT DOCUMENTS

| | | | |
|---|---|---|---|
| 4,717,765 A | 1/1988 | Hirao et al. | |
| RE33,047 E | 9/1989 | Miyake et al. | |
| 5,141,859 A * | 8/1992 | Niimi et al. ................... | 435/100 |
| 5,391,299 A | 2/1995 | Masuda et al. | |
| 5,873,943 A | 2/1999 | Magara et al. | |
| 6,120,612 A | 9/2000 | Mitsuhashi et al. | |
| 6,274,355 B1 | 8/2001 | Duflot et al. | |
| 6,284,498 B1 | 9/2001 | Fouache et al. | |
| 6,344,591 B2 * | 2/2002 | Leleu et al. ................... | 568/852 |
| 6,346,400 B1 | 2/2002 | Caboche | |

FOREIGN PATENT DOCUMENTS

| | | |
|---|---|---|
| JP | 60067000 | 4/1985 |
| JP | 62019210 | 1/1987 |
| JP | 2092296 | 4/1990 |
| JP | 2119789 | 5/1990 |
| JP | 9132587 | 5/1997 |

OTHER PUBLICATIONS

The American Heritage Dictiionary, entry for "immediately" (2000).*

* cited by examiner

*Primary Examiner* — David M Brunsman
(74) *Attorney, Agent, or Firm* — Fish & Richardson P.C.

(57) ABSTRACT

The current invention relates to a process for preparing maltitol enriched products and said process is chromatographically fractionating a maltose syrup followed by hydrogenating it into a liquid maltitol enriched product and optionally solidification or crystallization of maltitol. Liquid, solid and crystalline maltitol of different purities are obtainable by a single process.

7 Claims, No Drawings

US 7,935,190 B2

PROCESS FOR PREPARING MALTITOL ENRICHED PRODUCTS

CROSS-REFERENCE TO RELATED APPLICATIONS

This application is a National Stage application under 35 U.S.C. §371 and claims benefit under 35 U.S.C. §119(a) of International Application No. PCT/EP2004/007372 having an International Filing Date of Jul. 6, 2004, which claims the benefit of priority of EP 03254528.7 having a filing date of Jul. 18, 2003.

TECHNICAL FIELD

The present invention relates to a process for preparing liquid and/or solid products enriched with maltitol.

BACKGROUND

Maltitol or α-D-glucopyranosyl-4-D-sorbitol is the result of hydrogenation of maltose.

Numerous processes are known for the manufacture of maltose-rich and/or maltitol-rich syrups.

It is known to prepare anhydrous crystalline maltitol by inducing the crystallization of said maltitol in a syrup sufficiently rich in this product and sufficiently purified.

U.S. Pat No. 4,849,023 relates to a process for the preparation of a product with a high content of maltitol, characterized by catalytic hydrogenation of a maltose syrup, followed by chromatographic fractionation of the maltitol syrup formed during the hydrogenation step, and adjustment to the desired dry matter of at least the fraction enriched in maltitol.

U.S. Pat No. 4,846,139 relates to a process for the preparation of maltitol, comprising the successive steps of liquefying starch milk, saccharification of the liquefied starch, followed by catalytically hydrogenating with Ruthenium or Raney nickel catalysts to provide a maltitol syrup, and submitting said maltitol syrup to a chromatographic fractionation, crystallising the maltitol, and recycling the mother-liquors to the chromatographic fractionation step.

U.S. Pat. No. 6,284,498 covers a method of manufacturing a maltose-rich syrup having a maltose content of greater than 87%. The first step is liquefaction of a starch milk using alpha-amylase. After inhibiting the alpha-amylase there is a first saccharification step in the presence of a maltogenic alpha-amylase until the maltose content reaches or exceeds 75%. This is followed by a second saccharification step in the presence of a beta-amylase and at least one debranching enzyme selected from the group consisting of pullulanases and iso-amylases, to a maltose content of greater than 87%. The claims specifically require that these steps be carried out in this sequence.

U.S. Pat No. 6,346,400 covers a process for the preparation of a maltose rich syrup. It follows the process steps of liquefying a starch milk, followed by a saccharification step. The saccharification is carried out in the presence of a beta-amylase and at least one debranching enzyme selected from the group comprising pullulanases and iso-amylases. This step is followed by molecular sieving in order to collect a fraction enriched with maltose and a fraction enriched with glucose.

U.S. Pat No. 6,436,678 claims a method for preparing a maltose product. It involves treatment of a starch with an enzyme consisting essentially of beta-amylase. The treated starch contains amylose in an amount of 10 percent of greater, at least a portion of which becomes retrograded. At least a portion of the retrograded amylose is allowed to crystallize. The crystallized retrograded amylose is separated from the mixture.

U.S. Pat. No. 6,274,355 covers a method of manufacturing a maltose-rich syrup. It comprises the process steps of liquefying a starch milk and saccharification of the liquefied starch. The liquefied and saccharified starch milk is then brought into contact with an immobilized maltogenic alpha-amylase, which is immobilized on particles of a porous substrate.

U.S. Pat. No. 5,391,299 discloses a process for the production of starch sugars, and a maltose fraction with a maltose purity of at least 80% is obtained.

U.S. Pat. No. 6,284,498 relates to a method of manufacturing a maltose-rich syrup and said method is comprising a liquefaction of starch milk followed by a saccharification of the liquefied starch milk.

U.S. Pat. No. 5,932, 015 relates to a process for making crystalline maltitol and crystalline mixture solid. The process requires two chromatographic separation steps after the hydrogenation step. In the first chromatography step a fraction is obtained having a maltitol content of 80.5 to 86.5 percent; the second chromatography step yields a fraction with a maltitol content of 97.5 percent by weight or more.

U.S. Pat. No. 5,873,943 covers a process for manufacturing both crystalline maltitol and a crystalline mixture solid containing crystalline maltitol from the same raw material. It follows the process steps of hydrogenating a syrup having a high concentration of maltose, and chromatographically isolating a fraction having a high content of maltitol. Part of this fraction is crystallized, and another part is spray dried to create a crystalline mixture solid.

U.S. Pat. No. 6,120,612 covers a continuous manufacturing method for anhydrous crystalline maltitol. The process starts with a maltitol rich syrup, which is heated in a concentrating step, followed by a seed crystal addition and mixing step accompanied by more heating, to give a massecuite; and a crystal aging step where the massecuite is subjected to disintegration, mixing, stirring and transfer in an atmosphere in which temperature and moisture are adjusted to proceed the crystallization.

There is a further need for having a single process which is providing liquid, solid, and crystalline maltitol in different purities.

The current invention provides such a process.

SUMMARY OF INVENTION

The current invention relates to a process for preparing maltitol enriched products, and said process is comprising the successive steps:

a) obtaining syrup (A) containing at least 75%, preferably more than 80% of maltose based on dry substance, b) fractionating chromatographically, the process conditions of said fractionation are selected in order to obtain a fraction (B) rich in maltose, comprising at least 92% maltose based on dry substance of fraction (B), c) hydrogenating catalytically fraction (B) for obtaining a liquid maltitol product (C), d) increasing dry substance of liquid maltitol product (C), e) optionally solidifying or crystallizing.

The current invention relates to a process wherein the syrup (A) is obtained by liquefying starch milk to a dextrose equivalent of from 2 to 25 for obtaining liquefied starch milk and subjecting said liquefied starch milk to a saccharification step in presence of β-amylase and at least one debranching enzyme selected from the group consisting of pullulanases, iso-amylases and mixtures thereof, and optionally followed by addition of α-amylase for obtaining a syrup (A) containing at least 81% of maltose based on dry substance.

The current invention relates to a process wherein fraction (B) is comprising at least 93% maltose based on dry substance.

The current invention relates to a process wherein product (C) is comprising at least 90% maltitol (based on dry substance).

Furthermore, the current invention relates to a process in step d) of said process is followed by the further successive steps:
e) Crystallizing product (C) by one or multiple crystallization steps for obtaining crystalline maltitol intermediate (D) and liquid maltitol co-product (E), wherein intermediate (D) has a dry substance of at least 93%, and is comprising at least 97% maltitol based on dry substance, and
f) Drying crystalline maltitol intermediate (D) for obtaining crystalline maltitol product (F) of at least 98.5% dry substance, and comprising at least 97% maltitol based on dry substance.

The current invention further relates to a process wherein the co-product (E) is chromatographically fractionated, the process conditions of said fractionation are selected in order to obtain a fraction (G) rich in maltitol, comprising at least 90% maltitol based on dry substance.

The current invention further relates to a process wherein crystalline maltitol intermediate (D), co-product (E), and/or fraction (G) and optionally water are mixed for obtaining liquid maltitol product (H) containing at least 94% maltitol based on dry substance and having at least 50% dry substance.

The current invention relates to a process wherein crystalline maltitol (F) is having purity of at least 98%, preferably more than 99% purity, more preferably more than 99.5%.

DETAILED INVENTION

The current invention relates to a process for preparing maltitol enriched products, and said process is comprising the successive steps:
a) obtaining syrup (A) containing at least 75%, preferably more than 80% of maltose based on dry substance,
b) fractionating chromatographically, the process conditions of said fractionation are selected in order to obtain a fraction (B) rich in maltose, comprising at least 92% maltose based on dry substance of fraction (B),
c) hydrogenating catalytically fraction (B) for obtaining a liquid maltitol enriched product (C),
d) increasing dry substance of liquid maltitol product (C),
e) optionally solidifying or crystallizing.

The starch used as a base material for the syrup (A) is obtained from a source selected from the group consisting of leguminous starch, cereal starch, root starch, tuber starch, fruit starch, waxy type starches, high amylose starches, hybrid starches, and mixtures thereof. Suitable sources include corn, pea, potato, sweet potato, sorghum, banana, barley, wheat, rice, sago, amaranth, tapioca, arrowroot, canna, and waxy (containing at least about 95% by weight amylopectin) or high amylose (containing greater than 40% by weight amylose) varieties thereof.

The process conditions of the chromatographic fractionation include the elution rate, the supply rate with maltose syrup, temperature, the extraction rate of the fraction enriched with maltose syrup, the extraction rate of the fraction enriched with maltose and the composition of the desorption, adsorption and enrichment zones.

Any commercially available cation-exchange resin is suitable to be used in the chromatographic fractionation. In particular, a commercial available strong cation-exchange resin which is made of styrene-divinylbenzene bridge polymer combined with sulfonic group can be used. In a preferred embodiment, the cation exchange resin is applied in the sodium form for obtaining a fraction enriched in maltose.

The process conditions of the chromatographic fractionation are selected in such a way that the fraction (B) rich in maltose is comprising at least 92% maltose based on dry substance of fraction (B). Surprisingly the conditions and the cation exchange resin can be selected for obtaining fraction (B) which is containing more than 96% maltose based on dry substance of fraction (B). Preferably fraction (B) is containing more than 98% maltose based on dry substance of fraction (B). The maltose fraction (B) is containing at least 90%, preferably more than 95% at a dry substance of at least 30%, preferably at least 35%. Recovery of maltose in fraction (B) is at least 80%, preferably at least 85%. The co-product still can contain up to 40% or more maltose.

In a typical example a simulated moving bed is applied for the chromatographic fractionation. The dry substance of the supply syrup (A) is at least 50%, preferably 60%. The temperature of the chromatographic fractionation is higher than room temperature, preferably higher than 50° C., more preferably higher than 70° C.

The hydrogenation can be performed in presence of catalysts which are usually used for hydrogenating carbohydrates. In particular, commercially available Raney type nickel catalyst, supported nickel catalyst and re-activatable precious metal catalysts, such as ruthenium catalyst carried by activated carbon, are preferably used.

Any hydrogenation condition can be suitable in as far there is no decomposition of maltose taking place. Usually the hydrogenation step is conducted at hydrogen gas pressure of at least 10 bar, preferably between 30 to 200 bar and at a temperature of 90 to 150° C. so that the hydrogenation continues until the absorption of hydrogen gas stops.

In a further embodiment the supply syrup (B) can be used at dry substance of at least 50%, activated nickel catalyst is added and the hydrogenation is taking place at a temperature up to 135° C. and hydrogen pressure of at least 40 bar. The activated nickel catalyst is added in an amount of 4% on dry matter of supply syrup (B).

After the completion of absorption of hydrogen gas, e.g. after about 3 hours of hydrogenation, the hydrogenation catalyst (=activated nickel catalyst) is removed from the resulting liquid maltitol product (C). This syrup can be further decolorised and/or de-ionised by activated carbon or ion-exchange resin and/or polisher resins. The liquid maltitol product (C) is containing at least 92% maltitol, preferably at least 94%, more preferably at least 95% based on dry substance. After increasing the dry substance of the liquid product (C), the product can be stored and/or used as such.

Optionally the liquid product (C) is solidified for obtaining a solid maltitol product. Alternatively, the liquid product is crystallized by one or multiple crystallization steps for obtaining crystalline maltitol.

The current invention relates to a process wherein the syrup (A) is obtained by liquefying starch milk to a dextrose equivalent of from 2 to 25 for obtaining liquefied starch milk and subjecting said liquefied starch milk to a saccharification step in presence of β-amylase and at least one debranching enzyme selected from the group consisting of pullulanases, iso-amylases and mixtures thereof, and optionally followed by addition of α-amylase for obtaining a syrup (A) containing at least 81% of maltose based on dry substance.

D.E. or "dextrose equivalent" value is the reducing power of the starch hydrolysate expressed as D-glucose on the dry basis. The measurement of DE is based upon a titration method with Fehling's solutions.

The liquefaction may be done by acid or enzymatic treatment, preferably enzymatic liquefaction.

The parameters of the enzymatic saccharification, such as type of enzyme, origin of enzyme (vegetal or bacterial origin), appropriate combination with debranching enzymes, amount of enzyme, temperature of saccharification, and duration of said step, are selected in such a manner that the content of maltose is at least 81%, based on dry substance of syrup.

In a specific embodiment, the starch slurry is brought to a dry substance above 25% and a pH above 5.0, preferably above 5.5. The starch slurry is then treated with alpha amylase in a flash chamber at a temperature above 100° C. The holding time is less than 10 minutes at a temperature of at least 140° C. Additional alpha-amylase can be added and after a residence time of at least half an hour up to one hour, the starch slurry is converted into a product with DE of 4 to 5.

This product with DE of 4 to 5 can further be saccharified in presence of an 'enzyme cocktail' comprising β-amylases, pullullanase, and preferably a thermostable α-amylase. The conversion of product with DE of 4 to 5 into a maltose rich product is improved by adding alpha-amylase, preferably thermostable alpha-amylase. At a temperature of about 50° C., the total incubation time is somewhat more than 30 hours and the resulting syrup (A) is containing at least 81% maltose (based on dry substance).

Syrup (A) is subjected to chromatographic fractionation and the current invention further relates to a process wherein fraction (B) is comprising at least 93% maltose based on dry substance, preferably more than 96%, more preferably more than 98% maltose, based on dry substance.

This maltose enriched fraction (B) is subjected to hydrogenation and the current invention relates to a process wherein the hydrogenation product (C) is comprising at least 90% maltitol based on dry substance.

Furthermore, the current invention relates to a process wherein step d) of said process is followed by the further successive steps:
  e) Crystallizing product (C) by one or multiple crystallization steps for obtaining crystalline maltitol intermediate (D) and liquid maltitol co-product (E), wherein intermediate (D) has a dry substance of at least 93% and is comprising at least 97% maltitol based on dry substance,
  f) Drying crystalline maltitol intermediate (D) for obtaining crystalline maltitol product (F) of at least 98.5% dry substance, and comprising at least 97% maltitol based on dry substance.

The liquid maltitol co-product (E) is containing at least 70%, preferably 72% maltitol based on dry substance.

Product (F) can be re-crystallised for increasing the purity.

After having increased the dry substance of liquid maltitol product (C) above 50%, preferably above 60%, more preferably above 80%, the syrup is crystallised for obtaining a crystalline intermediate (D) and a liquid co-product (E).

In a specific embodiment, the syrup is concentrated to a concentration of greater than 85% dry solids. A specific cooling rate is applied and the crystallization is induced by agitation. The obtained crystals are preferably re-crystallised to increase the purity of the crystals above 99%, preferably 99.5%. The crystalline intermediate (D) is further converted into the final crystalline maltitol product (F) by further drying, eventually followed by sieving and packaging.

The recovery of maltitol enriched products can be increased either by crystallization of the mother liquor (co-product (E)) or by chromatographic fractionation of the mother liquor (co-product (E)). Preferably the quality of liquid co-product (E) is further improved by a chromatographic step whereby the process conditions are selected to convert the liquid co-product (E) into fraction (G) enriched in maltitol.

The dry substance of fraction (G) can be increased for obtaining a maltitol enriched syrup which can be used as such. Furthermore said fraction (G) can be solidified and/or crystallised.

Optionally a further grade of maltitol containing product (H) can be obtained by the current invention. Adding water to some maltitol containing products of the current invention, and mixing all or some of them will give product (H) at dry substance of at least 50% and which is containing at least 94% maltitol based on dry substance. Actually crystalline maltitol intermediate (D), co-product (E), and/or fraction (G) and optionally water are mixed for obtaining liquid maltitol product (H) containing at least 94% maltitol based on dry substance and having at least 50% dry substance.

In a specific embodiment the current invention relates to a process wherein
  a) starch milk is liquefied into a liquefied starch milk having a dextrose equivalent of from 2 to 25,
  b) liquefied starch milk is saccharified in presence of β-amylase, pullulanase and α-amylase for obtaining a maltose syrup (A) containing at least 81% maltose (based on dry substance),
  c) chromatographic fractionation for obtaining a maltose enriched fraction (B) containing at least 96% maltose, preferably 98% maltose (based on dry substance),
  d) hydrogenation of maltose enriched fraction (B) into a maltitol syrup (C) containing at least 95% maltitol (based on dry substance).

The maltitol syrup (C) can be used entirely for preparing either a liquid maltitol, crystalline maltitol or solidified maltitol.

Furthermore, the current invention relates to a process wherein crystalline maltitol (F) is having a purity of at least 98%, preferably more than 99% purity. In fact, purities of more than 99.5% and 99.7% are obtainable.

The current invention has the following advantages:
  A simple process which provides different maltitol enriched products; e.g. liquid maltitol, solidified maltitol and/or crystallised maltitol.
  Liquid maltitol syrups of different purities can be obtained, see for example product (C), and product (H).
  The same simple process allows obtaining crystalline maltitol with high recovery yields (60% and more) and high purity.
  The process further allows obtaining solidified maltitol products.
  Liquid, solid and crystalline maltitol of different purities are obtainable by a single process.
  Crystalline maltitol is direct obtainable after hydrogenation, no further chromatographic fractionation is required.
  The recovery yield of maltitol enriched product can be increased by chromatographic fractionation of the co-products formed, e.g. the mother liquor of the crystallization is further processed Surprisingly, it was found that high recovery yields of different maltitol products are achievable by having the liquefaction, saccharification immediately followed by chromatographic fractionation of maltose, and furthermore by having direct crystallisation of hydrogenated product.

Surprisingly, the current process allows obtaining different maltitol fractions in high recovery yields and high purity.

The current invention is illustrated by way of the following examples.

EXAMPLE

Liquefaction

A starch slurry at 27.5% dry substance and at pH of between 5.6-5.8 was treated with 0.042% alpha amylase (% on dry base) at 106° C. The holding time was 10-16 minutes and this holding time was followed by cooling to 100° C. in a flash chamber. In a second jet cooker a heat stock at temperature of 152° C. was given followed by holding time in coil for about 5 to 8 minutes and then cooling to 100° C.

Again 0.028% (based on dry base) of α-amylase was added.

After a residence time of 35 to 56 minutes the starch was converted in a product with DE (measured by tritation method in presence of Fehling's solutions) of 4 to 5. The α-amylase was deactivated at pH of 3.0 by addition of 2% HCl-solution.

After 20 minutes residence time the product was further cooled to 58-60° C. and pH was brought to 5.5 by adding 2% NaOH solution.

Saccharification

The previous liquefaction was followed by a saccharification step.

At pH 5.5 and temperature of 50° C. the following enzymes were added to the liquefied starch milk from th eliquefaction step:

- 0.10% (based on dry substance) β-amylase (Optimalt BBA)
- 0.10% (based on dry substance) pullullanase (Promozyme 400L)
- 0.030% (based on dry substance) β-amylase (Betalase 1500 EL)
- 0.05% (based on dry substance) thermostable α-amylase (BAN 480 L)

After a total incubation time of 32 hours the obtained saccharified product had the following composition (HPLC-analysis: Bio-Rad Aminex HPX-87; cation exchange column is the calcium form, column temperature: 80° C., Eluent Flow Rate: 0.6 ml/minute, column pressure limit: 1200 psi, injection volume: 20 μL, pressure control limit about 200 psi above the normal operating pressure of the column, eluent: degassed Milli-Q Purified water, detector: Differential refractometer).

| | |
|---|---|
| DP1: | 1.8% |
| DP2: | 81% |
| DP3: | 15% |
| $DP_{4+}$: | 17% |

Chromatographic Fractionation

The product with composition (DP1: 1.5%; DP2: 80.0%; DP3: 12.5% and $DP_{4+}$: 6%) was concentrated to 60% dry matter.

The concentrated product was applied at 75° C. onto a chromatographic equipment (ISMB) with ion exchange resin Dianion UBK 550 in Sodium form, for obtaining a fraction enriched in maltose. Said product had the following composition (DP1: 1.1%; DP2: 96%; DP3: 1.7%; $DP_{4+}$: 1.2%).

The co-product had the following composition: HPLC-analysis (Bio-Rad Aminex HPX-87, cation exchange column is the calcium form, column temperature: 80° C., Eluent Flow Rate: 0.6 ml/minute, column pressure limit: 1200 psi, injection volume: 20 μL, pressure control limit about 200 psi above the normal operating pressure of the column, eluent: degassed Milli-Q Purified water, detector: Differential refractometer) (DP1: 2.4%; DP2: 41.1%; DP3: 38.7%; $DP_{4+}$: 17.8%)

Further details are displayed in Table 1

TABLE 1

Results expressed per hour and per m³ of resin

| | | Feed | Product enriched in maltose | Co-product | Water |
|---|---|---|---|---|---|
| Composition (%) | DP1 | 1.5 | 1.1 | 2.4 | |
| | DP2 | 80.0 | 96.0 | 41.1 | |
| | DP3 | 12.5 | 1.7 | 38.7 | |
| | DP4+ | 6.0 | 1.2 | 17.8 | |
| Total weight (kg/h) | | 37.6 | 41.48 | 71.65 | 75.36 |
| Flow rate (L/h) | | 29.00 | 35.30 | 69.1 | 75.36 |
| % d.s. | | 60.0 | 38.5 | 9.2 | |

Hydrogenation 21.6 Kg (52% dry substance) of the fraction enriched in maltose having a composition (DP1: 1.1%; DP2: 96%; DP3: 1.7%; $DP_{4+}$: 1.2%) was charged into a stainless steel hydrogenation reactor. Activated nickel catalyst was added in an amount of 4% on dry matter of the fraction enriched in maltose and the suspension was vigorously stirred and heated up to 135° C. under hydrogen pressure of 43 bar. After 180 minutes of hydrogenation, the suspension was cooled to 90° C. and the catalyst was removed by settling and filtration. The aqueous solution at temperature of 40° C. was ion exchanged and polished over cationic and anionic resins and granular carbon. The product obtained had the following composition (HPLC analysis: Bio-Rad Aminex HPX-87, cation exchange column is the calcium form, column temperature: 80° C., Eluent Flow Rate: 0.6 ml/minute, column pressure limit: 1200 psi, injection volume: 20 μL, pressure control limit about 200 psi above the normal operating pressure of the column, eluent: degassed Milli-Q Purified water, detector: Differential refractometer)

| | |
|---|---|
| DP1: | 2.1% |
| DP2: | 94.8% |
| DP3: | 1.5% |
| $DP_{4+}$: | 1.2% |
| Others: | 0.4% |

Crystallisation

16 Kg of the maltitol product (composition: DP1: 2.1%, DP2: 94.8%, DP3: 1.5%, DP4+: 1.2%, others: 0.4%) was evaporated at 80° C. to a concentration of greater than 85% dry solids. The crystallisers were filled at 80° C. and cooled to 35° C. at a rate of 0.83° C. per hour. Crystallisers were at maximum agitation.

After reaching temperature set point (35° C.), 5% by weight cold water (approx. 20° C.) is added to the magma to reduce viscosity for pumping and centrifuge washing.

Centrifuged crystals were washed with a 15% by weight water.

Washed crystals with a purity of approximately 98% by weight were melted in hot water (80° C.) at a concentration of greater than 85% dry solids.

This concentrated maltitol liquid was fed to the secondary crystallisers. The crystallisers were filled at 80° C. and cooled to 40° C. at a rate of 1° C. per hour.

Crystal aggregates were washed at 20° C. with a 25% by weight water.

Washed crystals (5.33 Kg) had a purity of greater than 99.5% dry basis and a moisture of about 3%. (Recovery yield: 65%)

Crystals were dried, sieved, and packaged.

9.76 Kg of mother liquor from the first crystallization had a purity of 91% maltitol. Mother liquor was concentrated to 85% dry solids. The crystallisers were filled at 80° C. and cooled to 35° C. at a rate of 0.6° C. per hour. Crystallisers were at maximum agitation. After reaching temperature set point (35° C.), 5% by weight cold water (approx. 20° C.) is added to the magma to reduce viscosity for pumping and centrifuge washing. Crystal aggregates were washed at 20° C. with a 15% by weight water.

Washed crystals with a purity of approximately 97% maltitol by weight are melted in hot water (80° C.) at a concentration of greater than 85% dry solids and added to the secondary crystalliser feed.

The invention claimed is:

1. Process for preparing maltitol enriched products, said process consisting essentially of the successive steps:
    a) liquefying starch milk to a dextrose equivalent of from 2 to 25 and subjecting said liquefied starch milk to a saccharification step in the presence of beta-amylase and at least one debranching enzyme selected from the group consisting of pullulanases, iso-amylases and mixtures thereof, followed by the addition of alpha-amylase for obtaining syrup (A) containing at least 81% of maltose based on dry substance,
    b) fractionating said syrup (A) chromatographically, wherein the process conditions of said fractionation are selected in order to obtain a fraction (B) rich in maltose, wherein said fraction (B) comprises at least 96% maltose based on dry substance of fraction (B), wherein the recovery of maltose in fraction (B) is at least 80%,
    c) catalytically hydrogenating fraction (B) to obtain a liquid maltitol enriched product (C) comprising at least 94% maltitol, and
    d) increasing dry substance of liquid maltitol enriched product (C).

2. A process for preparing maltitol enriched products, said process consisting essentially of the successive steps:
    a) liquefying starch milk to a dextrose equivalent of from 2 to 25 and subjecting said liquefied starch milk to a saccharification step in the presence of beta-amylase and at least one debranching enzyme selected from the group consisting of pullulanases, iso-amylases and mixtures thereof, followed by the addition of alpha-amylase for obtaining syrup (A) containing at least 81% of maltose based on dry substance,
    b) fractionating said syrup (A) chromatographically, wherein the process conditions of said fractionation are selected in order to obtain a fraction (B) rich in maltose, wherein said fraction (B) comprises at least 96% maltose based on dry substance of fraction (B), wherein the recovery of maltose in fraction (B) is at least 80%,
    c) catalytically hydrogenating fraction (B) to obtain a liquid maltitol enriched product (C) comprising at least 94% maltitol,
    d) increasing dry substance of liquid maltitol enriched product (C),
    e) crystallizing product (C) by one or multiple crystallization steps to obtain crystalline maltitol intermediate (D) and liquid maltitol co-product (E), wherein intermediate (D) has a dry substance of at least 93% and comprises at least 97% maltitol based on dry substance, and
    f) drying crystalline maltitol intermediate (D) to obtain crystalline maltitol product (F) of at least 98.5% dry substance and comprising at least 97% maltitol based on dry substance.

3. A process according to claim 2 characterized in that crystalline maltitol (F) has a purity of at least 98%.

4. A process according to claim 2 characterized in that crystalline maltitol (F) has a purity of at least 99%.

5. A process according to claim 2 characterized in that crystalline maltitol (F) has a purity of at least 99.5%.

6. A process for preparing maltitol enriched products, said process consisting essentially of the successive steps:
    a) liquefying starch milk to a dextrose equivalent of from 2 to 25 and subjecting said liquefied starch milk to a saccharification step in the presence of beta-amylase and at least one debranching enzyme selected from the group consisting of pullulanases, iso-amylases and mixtures thereof, followed by the addition of alpha-amylase for obtaining syrup (A) containing at least 81% of maltose based on dry substance,
    b) fractionating said syrup (A) chromatographically, wherein the process conditions of said fractionation are selected in order to obtain a fraction (B) rich in maltose, wherein said fraction (B) comprises at least 96% maltose based on dry substance of fraction (B), wherein the recovery of maltose in fraction (B) is at least 80%,
    c) catalytically hydrogenating fraction (B) to obtain a liquid maltitol enriched product (C) comprising at least 94% maltitol,
    d) increasing dry substance of liquid maltitol enriched product (C),
    e) crystallizing product (C) by one or multiple crystallization steps to obtain crystalline maltitol intermediate (D) and liquid maltitol co-product (E), wherein intermediate (D) has a dry substance of at least 93% and comprises at least 97% maltitol based on dry substance,
    f) drying crystalline maltitol intermediate (D) to obtain crystalline maltitol product (F) of at least 98.5% dry substance and comprising at least 97% maltitol based on dry substance, and
    g) fractionating chromatographically the liquid maltitol co-product (E), wherein the process conditions of said fractionation are selected in order to obtain a fraction (G) rich in maltitol, said fraction comprising at least 90% maltitol based on dry substance.

7. A process according to claim 6 characterized in that crystalline maltitol intermediate (D), co-product (E), and/or fraction (G) and optionally water are mixed to obtain liquid maltitol product (H) containing at least 94% maltitol based on dry substance and having at least 50% dry substance.

* * * * *

UNITED STATES PATENT AND TRADEMARK OFFICE
CERTIFICATE OF CORRECTION

| | | |
|---|---|---|
| PATENT NO. | : 7,935,190 B2 | |
| APPLICATION NO. | : 10/564652 | |
| DATED | : May 3, 2011 | |
| INVENTOR(S) | : Robert Henri-Marcel Stouffs et al. | |

It is certified that error appears in the above-identified patent and that said Letters Patent is hereby corrected as shown below:

On the Title Page, Item (75) Inventors, Riccardo Sacrato, please delete "Lendianara" and insert --Lendinara-- therefor;

On the Title Page, Item (56) References Cited, Other Publications, The American Heritage Dictiionary entry, please delete "Dictiionary" and insert --Dictionary-- therefor.

Signed and Sealed this
Twenty-fifth Day of October, 2011

David J. Kappos
*Director of the United States Patent and Trademark Office*